United States Patent [19]

Lesher et al.

[11] 4,363,911

[45] Dec. 14, 1982

[54] 1,2-DIHYDRO-6-[2-(DIMETHYLAMINO)E-THENYL]-2-OXO-5-(PYRIDINYL) NICOTINONITRILES

[75] Inventors: George Y. Lesher, Schodack; Ruth P. Brundage, East Greenbush, both of N.Y.

[73] Assignee: Sterling Drug Inc., New York, N.Y.

[21] Appl. No.: 298,935

[22] Filed: Sep. 3, 1981

[51] Int. Cl.$^3$ .......................................... C07D 401/04
[52] U.S. Cl. .................................................. 546/257
[58] Field of Search ................. 546/257, 256; 424/263

[56] References Cited
U.S. PATENT DOCUMENTS 4,004,012  1/1977  Lesher et al. ...................... 546/257
4,276,293  6/1981  Lesher et al. ...................... 424/263

FOREIGN PATENT DOCUMENTS 886336  5/1980  Belgium .

*Primary Examiner*—John M. Ford
*Attorney, Agent, or Firm*—Robert K. Bair; B. Woodrow Wyatt

[57] ABSTRACT

1-$R_1$-1,2-dihydro-6-[2-(dimethylamino)ethenyl]-2-oxo-5-PY-nicotinonitriles, where $R_1$ is hydrogen or methyl, and PY is 4- or 3-pyridinyl or 4- or 3-pyridinyl having one or two lower-alkyl substituents, or pharmaceutically acceptable acid-addition salts thereof are useful as cardiotonic agents. Said compounds are prepared by reacting 1,2-dihydro-6-methyl-2-oxo-5-PY-nicotinonitrile with dimethylformamide dimethylacetal. Shown is the cardiotonic use of said compounds or pharmaceutically acceptable acid-addition salts thereof.

4 Claims, No Drawings

1,2-DIHYDRO-6-[2-(DIMETHYLAMINO)E-THENYL]-2-OXO-5-(PYRIDINYL) NICOTINONITRILES

BACKGROUND OF THE INVENTION (a) Field of the Invention

This invention relates to 1,2-dihydro-6-substituted-2-oxo-5-(pyridinyl)nicotinonitrile derivatives, their use as a cardiotonic agents, and their preparation.

(b) Description of the Prior Art

Belgian Pat. No. 886,336, granted May 25, 1980, shows, inter alia, 1,2-dihydro-6-methyl-2-oxo-5-(pyridinyl)nicotinonitriles as cardiotonic agents. These compounds also are disclosed and claimed in copending Lesher and Philion U.S. patent application Ser. No. 198,461, filed Oct. 20, 1980 and now U.S. Pat. No. 4,313,951 issued Feb. 2, 1982, a continuation-in-part of application Serial No. 97,504, filed Nov. 26, 1979 and now abandoned.

Lesher, Opalka and Page U.S. Pat. No. 4,276,293, issued June 30, 1981, discloses inter alia as intermediates 1,2-dihydro-6-methyl-2-oxo-5-(pyridinyl)nicotinonitriles.

SUMMARY OF THE INVENTION

In a composition of matter aspect, the invention resides in the compound, $1-R_1$-1,2-dihydro-6-[2-(dimethylamino)ethenyl]-2-oxo-5-PY-nicotinonitrile or acid-addition salt thereof, useful as a cardiotonic agent, where $R_1$ and PY are defined hereinbelow.

In a process aspect the invention comprises reacting 1,2-dihydro-6-methyl-2-oxo-5-PY-nicotinonitrile with dimethylformamide dimethylacetal to produce 6-[2-(dimethylamino)-ethenyl]-1-methyl-2-oxo-5-PY-nicotinonitrile and/or a mixture of 1,2-dihydro-1,6-dimethyl-2-oxo-5-PY-nicotinonitrile and 6-[2-(dimethylamino)ethenyl]-2-oxo-5-PY-nicotinonitrile and separating the said products where two or more are present.

A composition aspect of the invention resides in a cardiotonic composition for increasing cardiac contractility, said composition comprising a pharmaceutically acceptable carrier and, as the active ingredient thereof, a cardiotonically effective amount of $1-R_1$-1,2-dihydro-6-[2-(dimethylamino)ethenyl]-2-oxo-5-PY-nicotinonitrile or pharmaceutically acceptable acid-addition salt thereof.

In a method aspect the invention relates to a method for increasing cardiac contractility in a patient requiring such treatment which comprises administering a medicament comprising a pharmaceutically acceptable carrier and, as the active component thereof, a cardiotonically effective amount of $1-R_1$-1,2-dihydro-6-[2-(dimethylamino)ethenyl]-2-oxo-5-PY-nicotinonitrile or pharmaceutically acceptable acid-addition salt thereof.

DETAILED DESCRIPTION INCLUSIVE OF PREFERRED EMBODIMENTS

In a composition of matter aspect the invention resides in $1-R_1$-1,2-dihydro-6-[2-(dimethylamino)ethenyl]-2-oxo-5-PY-nicotinonitrile having the formula I

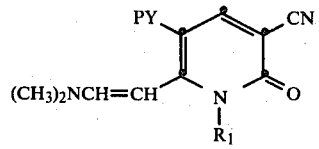

or acid-addition salt thereof, where $R_1$ is hydrogen or methyl, and PY is 4-pyridinyl or 3-pyridinyl, or 4-pyridinyl or 3-pyridinyl having one or two lower-alkyl substituents. Preferred embodiments are the compounds of formula I where PY is 4- or 3-pyridinyl and $R_1$ is methyl. A particularly preferred embodiment is the compound of formula I where PY is 4-pyridinyl and $R_1$ is methyl. The compounds of formula I are useful as cardiotonic agents, as determined by standard pharmacological evaluation procedures.

A process aspect of the invention resides in the process which comprises reacting 1,2-dihydro-6-methyl-2-oxo-5-PY-nicotinonitrile with dimethylformamide dimethylacetal to produce the compound having formula I where $R_1$ is methyl and/or a mixture of the compound having formula I where $R_1$ is hydrogen and 1,2-dihydro-1,6-dimethyl-2-oxo-5-PY-nicotinonitrile and where two or more products are produced separating each product. A preferred embodiment of this process aspect of the invention comprises reacting 1,2-dihydro-6-methyl-2-oxo-5-(4-pyridinyl)nicotinonitrile with three or more molar equivalents of dimethylacetamide dimethylacetal to produce 1,2-dihydro-6-[2-dimethylamino)ethenyl]-1-methyl-2oxo-5-(4-pyridinyl)nicotinonitrile.

A composition aspect of the invention resides in the cardiotonic composition for increasing cardiac contractility, said composition comprising a pharmaceutically acceptable carrier and, as the active component thereof, a cardiotonically effective amount of the compound having formula I or a pharmaceutically acceptable acid-addition salt thereof.

A method aspect of the invention resides in the method for increasing cardiac contractility in a patient requiring such treatment which comprises administering orally or parenterally in solid or liquid dosage form to such patient a cardiotonically effective amount of the compound of formula I or pharmaceutically acceptable acid-addition salt thereof.

Illustrative of PY in formula I where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds having formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds having formula I were assigned on the basis of evidence provided by infrared, nuclear magnetic resonance and mass spectra, by chromatographic mobilities, and, by the correspondence of calculated and found values for the elementary analyses.

The manner of making and using the instant invention will now be generally described so as to enable a person skilled in the art of pharmaceutical chemistry to make and use the same, as follows.

The reaction of 1,2-dihydro-6-methyl-2-oxo-5-PY-nicotinonitrile with dimethylformamide dimethylacetal to product 1,2-dihydro-6-[2-(dimethylamino)ethenyl]-1-methyl-2-oxo-5-PY-nicotinonitrile and/or a mixture of 1,2-dihydro-6-[2-(dimethylamino)ethenyl]-2-oxo-5-PY-nicotinonitrile and 1,2-dihydro-1,6-dimethyl-2-oxo-5-PY-nicotinonitrile is carried out by heating the reactants at about 60° C. to 120° C., preferably about 75° C. to 85° C. in an aprotic solvent, preferably acetonitrile or dimethylformamide. Other suitable aprotic solvents include dioxane, tetrahydrofuran, 1,2-dimethoxyethane, toluene, and the like. The quantities of the three products obtained by the process varies depending upon the molar ratio of reactants used. The quantity of 1,2-dihydro-6-[2-(dimethylamino)ethenyl]-1-methyl-2-oxo-5-PY-nicotinonitrile (I, $R_1$ is methyl) is increased as the proportion of dimethylformamide dimethylacetal to 1,2-dihydro-6-methyl-2-oxo-5-PY-nicotinonitrile becomes greater. For example, as seen in Example 2 hereinbelow where the product of formula I where $R_1$ is hydrogen is readily isolated, slightly more than molar excess of dimethylformamide dimethylacetal is used; and, as seen in Example 1 hereinbelow where the product of formula I where $R_1$ is methyl is crystallized from the reaction mixture and none of the other two products is formed in sufficient quantities to be isolated, a three to one molar excess of dimethylformamide dimethylacetal is used. The third product and major component in Example 2, that is, 1,2-dihydro-1,6-dimethyl-2-oxo-5-PY-nicotinonitrile, is obtained from the filtrate after removal of the compound of formula I where $R_1$ is hydrogen. Separation of the products where two or more are present can be carried out as illustrated in Examples 1 and 2 or by any other conventional means, e.g., fractional crystallization, fractional extraction, or the like.

The following examples will further illustrate the invention without, however, limiting it thereto.

EXAMPLE 1

6-[2-(Dimethylamino)ethenyl]-1,2-dihydro-1-methyl-2-oxo-5-(4-pyridinyl)nicotinonitrile A mixture containing 49 g. (0.23 mole) of 1,2-dihydro-6-methyl-2-oxo-5-(4-pyridinyl)nicotinonitrile, 100 ml. (0.75 mole) of dimethylformamide dimethylacetal and 2.4 liters of acetonitrile was refluxed with stirring for two hours during which a solution resulted. The reaction solution was then concentrated to about 20% of its original volume and filtered while hot to give 10.1 g. of slightly impure 6-[2-(dimethylamino)ethenyl]-1,2-dihydro-1-methyl-2-oxo-5-(4-pyridinyl)-nicotinonitrile, m.p. 215°–217° C. The filtrate was chilled and the crystalline product that separated was collected and dried to yield 13.6 g. of pure 6-[2-(dimethylamino)ethenyl]-1,2-dihydro-1-methyl-2-oxo-5-(4-pyridinyl)nicotinonitrile, m.p. 216°–218° C.

Acid-addition salts of 6-[2-(dimethylamino)-ethenyl]-1,2-dihydro-1-methyl-2-oxo-5-(4-pyridinyl)nicotinonitrile are conveniently prepared by carefully adding to a mixture of 1 g. of 6-[2-(dimethylamino)ethenyl]-1,2-dihydro-1-methyl-2-oxo-5-(4-pyridinyl)nicotinonitrile in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 6-[2-(dimethylamino)-ethenyl]-1,2-dihydro-1-methyl-2-oxo-5-(4-pyridinyl)nicotinonitrile and the appropriate acid, e.g., lactic acid or hydrochloric acid to prepare respectively the monolactate or monohydrochloride salt in aqueous solution.

EXAMPLE 2

6-[2-(Dimethylamino)ethenyl]-1,2-dihydro-2-oxo-5-(4-pyridinyl)nicotinonitrile

A mixture containing 21.4 g. (0.10 mole) of 1,2-dihydro-6-methyl-2-oxo-5-(4-pyridinyl)-nicotinonitrile, 14.9 g. (0.125 mole) of dimethylformamide dimethylacetal and 1 liter of acetonitrile was refluxed with stirring for about three hours and fifteen minutes. The reaction mixture was allowed to cool to room temperature and was filtered. The filtercake was recrystallized from dimethylformamide to yield 2.4 g. of 6-[2-(dimethylamino)ethenyl]-1,2-dihydro-2-oxo-5-(4-pyridinyl)-nicotinonitrile, m.p. >300° C. The reaction mixture (acetonitrile) filtrate was concentrated in vacuo and the residue was recrystallized from about 100 ml. of acetonitrile to produce 8.0 g. of solid whose major component was 1,2-dihydro-1,6-dimethyl-2-oxo-5-(4-pyridinyl)nicotinonitrile and which also contained some 6-[2-(dimethylamino)ethenyl]-1,2-dihydro-1-methyl-2-oxo-5-(4-pyridinyl)nicotinonitrile, the presence of each shown by their nuclear magnetic resonance (n.m.r.) spectra in dimethyl sulfoxide. Said 1,6-dimethyl compound was purified by a second recrystallization from acetonitrile and then suspending the resulting 5.3 g. of solid in a mixture of 30 ml. of water and 5 ml. of 2 N aqueous potassium hydroxide solution, collecting the insoluble material, drying it; and, then recrystallizing it from dimethylformamide, collecting it by filtering the recrystallizing mixture at about 50° C. and drying the product to obtain about 1.5 g. of 1,2-dihydro-1,6-dimethyl-2-oxo-5-(4-pyridinyl)nicotinonitrile, m.p. 246°–249° C. A mixed melting point of this 1,6-dimethyl compound with a sample of the same compound prepared by another and preferred method, that is, by reacting 1-(4-pyridinyl)-2-(dimethylamino)ethenyl methyl ketone with N-methyl-α-cyanoacetamide and sodium methoxide in methanol [Example B-4, U.S. Pat. application Ser. No. 198,461] showed no depression and their n.m.r. spectra were the same.

Acid-addition salts of 6-[2-(dimethylamino)ethenyl]-1,2-dihydro-2-oxo-5-(4-pyridinyl)nicotinonitrile are conveniently prepared by carefully adding to a mixture of 1 g. of 6-[2-(dimethylamino)ethenyl]-1,2-dihydro-2-oxo-5-(4-pyridinyl)nicotinonitrile in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 6-[2-(dimethylamino)ethenyl]-1,2-dihydro-2-oxo-5-(4-pyridinyl)nicotinonitrile and the appropriate acid, e.g., lactic acid or hydrochloric acid to prepare respectively the monolactate or monohydrochloride in aqueous solution.

Following the procedure described in Example 1 but using in place of 1,2-dihydro-6-methyl-2-oxo-5-(4-pyridinyl)-nicotinonitrile a molar equivalent quantity of the appropriate 1,2-dihydro-6-methyl-2-oxo-5-PY-nicotinonitrile, it is contemplated that the following 6-[2-(dimethylamino)ethenyl]-1,2-dihydro-1-methyl-2-oxo-5-PY-nicotinonitriles of Examples 3–8 can be obtained.

3. 6-[2-(Dimethylamino)ethenyl]-1,2-dihydro-1-methyl-2-oxo-5-(3-pyridinyl)nicotinonitrile.

4. 6-[2-(Dimethylamino)ethenyl]-1,2-dihydro-1-methyl-2-oxo-5-(2-methyl-4-pyridinyl)nicotinonitrile.

5. 6-[2-(Dimethylamino)ethenyl]-1,2-dihydro-1-methyl-2-oxo-5-(2-methyl-3-pyridinyl)nicotinonitrile.

6. 6-[2-(Dimethylamino)ethenyl]-1,2-dihydro-1-methyl-2-oxo-5-(5-methyl-3-pyridinyl)nicotinonitrile.

7. 6-[2-(Dimethylamino)ethenyl]-1,2-dihydro-1-methyl-2-oxo-5-(3-ethyl-4-pyridinyl)nicotinonitrile.

8. 6-[2-(Dimethylamino)ethenyl]-1,2-dihydro-1-methyl-2-oxo-5-(2,6-dimethyl-4-pyridinyl)nicotinonitrile.

Following the procedure described in Example 2 but using in place of 1,2-dihydro-6-methyl-2-oxo-5-(4-pyridinyl)nicotinonitrile a molar equivalent quantity of the appropriate 1,2-dihydro-6-methyl-2-oxo-5-PY-nicotinonitrile, it is contemplated that the following 6-[2-(dimethylamino)ethenyl]-1,2-dihydro-2-oxo-5-PY-nicotinonitriles of Examples 9–14 can be obtained.

9. 6-[2-(Dimethylamino)ethenyl]-1,2-dihydro-2-oxo-5-(3-pyridinyl)nicotinonitrile.

10. 6-[2-(Dimethylamino)ethenyl]-1,2-dihydro-2-oxo-5-(2-methyl-3-pyridinyl)nicotinonitrile.

11. 6-[2-(Dimethylamino)ethenyl]-1,2-dihydro-2-oxo-5-(5-methyl-3-pyridinyl)nicotinonitrile.

12. 6-[2-(Dimethylamino)ethenyl]-1,2-dihydro-2-oxo-5-(3-methyl-4-pyridinyl)nicotinonitrile.

13. 6-[2-(Dimethylamino)ethenyl]-1,2-dihydro-2-oxo-5-(2-methyl-4-pyridinyl)nicotinonitrile.

14. 6-[2-(Dimethylamino)ethenyl]-1,2-dihydro-2-oxo-5-(2,6-dimethyl-4-pyridinyl)nicotinonitrile.

The usefulness of the compounds of formula I or their pharmaceutically acceptable acid-addition salts as cardiotonic agents is demonstrated by their effectiveness in standard pharmacological test procedures, for example, in causing a significant increase in the contractile force of the isolated cat or guinea pig atria and papillary muscle and in causing a significant increase in the cardiac contractile force in the anesthetized dog with low or minimal changes in heart rate and blood pressure. These test procedures are described in the U.S. Pat. No. 4,072,746, issued Feb. 7, 1980.

When tested by the above-described isolated cat or guinea pig atria and papillary muscle procedure at doses of 30 and/or 100 μg./ml., the compounds of formula I were found to cause a significant increase, that is, greater than 25% or 30% in papillary muscle force, and a significant increase, that is, greater than 25% or 30% in right atrial force, while causing only a low percentage increase (about one-third or less than the percentage increase in right atrial or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, the percentage increases in guinea pig papillary muscle force and right atrial force for 6-[2-(dimethylamino)ethenyl]-1,2-dihydro-2-oxo-5-(4-pyridinyl)nicotinonitrile, Example 2 herein, were found to be 56% and 30% respectively when tested at 30 μg./ml. and 83% and 35% respectively at 100 μg./ml. Similarly, the percentage increases in guinea pig papillary muscle force and right atrial force for 6-[2-(dimethylamino)ethenyl]-1,2-dihydro-1-methyl-2-oxo-5-(4-pyridinyl)nicotinonitrile, Example 1 herein, were found to be 94% and 124% respectively at 100 μg./ml.

The present invention includes within its scope a cardiotonic composition for increasing cardiac contractility, said composition comprising a pharmaceutically acceptable carrier and, as the active component thereof, the cardiotonic compound of formula I or pharmaceutically acceptable acid-addition salt thereof. The invention also includes within its scope the method for increasing cardiac contractility in a patient requiring such treatment which comprises administering to such patient a cardiotonically effective amount of said compound of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commmonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example, by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgment on the patient's behalf.

We claim:

1. A compound having the formula

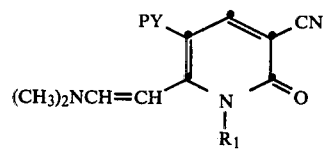

or acid-addition salt thereof, where $R_1$ is hydrogen or methyl, and PY is 4-pyridinyl or 3-pyridinyl, or 4-pyridinyl or 3-pyridinyl having one or two lower-alkyl substituents.

2. A compound according to claim 1 where PY is 4- or 3-pyridinyl and $R_1$ is methyl.

3. 1,2-Dihydro-6-[2-(dimethylamino)ethenyl]-1-methyl-2-oxo-5-(4-pyridinyl)nicotinonitrile according to claim 1 or acid-addition salt thereof.

4. 1,2-Dihydro-6-[2-(dimethylamino)ethenyl]-2-oxo-5-(4-pyridinyl)nicotinonitrile according to claim 1 or acid-addition salt thereof.

* * * * *

UNITED STATES PATENT AND TRADEMARK OFFICE
CERTIFICATE OF CORRECTION

PATENT NO. : 4,363,911

DATED : December 14, 1982

INVENTOR(S) : G. Y. Lesher et al.

It is certified that error appears in the above-identified patent and that said Letters Patent is hereby corrected as shown below:

Column 1, line 12, delete "a".

Column 2, line 33, "2oxo" should read -- 2-oxo --.

Column 2, line 53, "2,-dimethyl-" should read -- 2,3-dimethyl- --.

Column 3, line 45, "product" should read -- produce --.

Column 7, line 8, "commmonly" should read -- commonly --.

Signed and Sealed this

Fifteenth Day of May 1984

[SEAL]

Attest:

Attesting Officer

GERALD J. MOSSINGHOFF

Commissioner of Patents and Trademarks